(12) United States Patent
Lee (10) Patent No.: US 12,171,896 B2
(45) Date of Patent: Dec. 24, 2024

(54) HAND SANITIZING APPARATUS AND METHOD FOR A VEHICLE

(71) Applicants: HYUNDAI MOTOR COMPANY, Seoul (KR); KIA CORPORATION, Seoul (KR)

(72) Inventor: Kwang-Soon Lee, Seoul (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 824 days.

(21) Appl. No.: 17/384,113

(22) Filed: Jul. 23, 2021

(65) Prior Publication Data
US 2022/0175995 A1 Jun. 9, 2022

(30) Foreign Application Priority Data
Dec. 9, 2020 (KR) .................. 10-2020-0171352

(51) Int. Cl.
*A61L 2/24* (2006.01)
*A61L 2/00* (2006.01)
*B60R 15/00* (2006.01)

(52) U.S. Cl.
CPC .............. *A61L 2/24* (2013.01); *A61L 2/0088* (2013.01); *B60R 15/00* (2013.01); *A61L 2202/16* (2013.01); *A61L 2209/134* (2013.01)

(58) Field of Classification Search
CPC . A61L 2/24; A61L 2/0088; A61L 2/22; A61L 2209/134; A61L 2202/15; A61L 2202/16; B60R 15/00
See application file for complete search history.

(56) References Cited

U.S. PATENT DOCUMENTS

| | | | |
|---|---|---|---|
| 11,559,596 B2* | 1/2023 | Harris | E05B 1/0069 |
| 11,684,684 B2* | 6/2023 | De Francesco | E05B 85/10 422/24 |
| 11,897,515 B2* | 2/2024 | McKnew | G06Q 50/40 |
| 12,005,834 B2* | 6/2024 | Kyle | B60Q 1/0023 |
| 2017/0129396 A1* | 5/2017 | Salter | A61L 2/10 |
| 2021/0346545 A1* | 11/2021 | Carlin | A61L 9/20 |
| 2021/0393831 A1* | 12/2021 | Harris | E05B 85/16 |
| 2022/0062465 A1* | 3/2022 | De Francesco | E05B 85/10 |
| 2022/0062475 A1* | 3/2022 | Johnson | A61L 2/22 |
| 2022/0332291 A1* | 10/2022 | Goemer | A47L 9/2821 |

(Continued)

FOREIGN PATENT DOCUMENTS

KR 20000010757 U 6/2000

*Primary Examiner* — Shogo Sasaki
(74) *Attorney, Agent, or Firm* — Lempia Summerfield Katz LLC (57) ABSTRACT

The present disclosure provides a hand sanitizing apparatus able to automatically prevent the inside of a vehicle from being contaminated by at least one of bacterium and virus by a typical pattern of behaviors of an occupant. A communicator performs pairing with a smart key. A first sensor system detects whether or not a portion of a hand of an occupant enters an inside of a door handle after the pairing. A second sensor system detects a contact position of the portion of the hand in response to the detection of the first sensor system. A controller determines a spray area onto which a sanitizer is to be sprayed in accordance with the contact position. A drive unit sprays the sanitizer onto the spray area determined by an instrument unit provided on the door handle.

20 Claims, 9 Drawing Sheets

(56) References Cited

U.S. PATENT DOCUMENTS

| | | | |
|---|---|---|---|
| 2023/0201397 A1* | 6/2023 | Roberge | G07C 9/00174 |
| 2023/0211756 A1* | 7/2023 | McKnew | G05D 1/0297 |
| | | | 422/28 |
| 2023/0256124 A1* | 8/2023 | Gardiner | A61L 2/24 |
| | | | 250/454.11 |

* cited by examiner

FIG.9

HAND SANITIZING APPARATUS AND METHOD FOR A VEHICLE

BACKGROUND OF THE DISCLOSURE

Field of the Disclosure

The present disclosure relates to a hand sanitizing technology for a vehicle, and particularly, to a hand sanitizing apparatus and a method for automatically preventing the inside of a vehicle from being contaminated by at least one of bacterium and virus by a typical pattern of behaviors of an occupant.

Description of Related Art

In general, in accordance with survey reporting that it is difficult to terminate coronavirus disease 2019 (COVID-19) in the future, everyone deeply agrees in the importance of cleanliness, such as hand sanitization, due to concerns about variant viruses or novel viruses. The necessity of hand sanitization had been a great issue during the severe acute respiratory syndrome (SARS) outbreak, during which demand for automatic foam soap instead of solid soap surged.

Currently, in a case of entering a building, hand sanitization is autonomously performed at the entrance of the building in order to prevent the indoor space from being contaminated. However, in a case in which an occupant enters a vehicle after having contacted a contaminated environment outside the vehicle, prevention is difficult without the care of the occupant.

This is because, when the occupant returns to the vehicle after having used a common use article, such as a cart, used a common facility, such as an escalator, or bought displayed goods during shopping in a shopping mall, a hand of the occupant may have primarily been exposed to invisible contamination.

Accordingly, hand sanitization that the occupant may think bothersome or tend to forget may be provided as a regular service without adding further action to previous actions that the occupant performs when entering the vehicle.

Specifically, a system enabling an intelligent vehicle to manage and protect the health of a vehicle occupant is essentially required.

SUMMARY OF THE DISCLOSURE

Accordingly, an object of the present disclosure considering the above point is to provide a hand sanitizing apparatus and a method able to automatically prevent the inside of a vehicle from being contaminated by at least one of bacterium or virus by typical pattern of behavior of an occupant.

In order to achieve the above objective, the present disclosure provides a hand sanitizing apparatus for a vehicle. The hand sanitizing apparatus is able to automatically prevent the inside of a vehicle from being contaminated by at least one of bacterium or virus by a typical pattern of behavior of an occupant.

As an embodiment, the hand sanitizing apparatus may include: a communicator performing pairing with a smart key; a first sensor system detecting whether or not a portion of a hand of an occupant enters an inside of a door handle after the pairing; a second sensor system detecting a contact position of the portion of the hand in response to the detection of the first sensor system; a controller determining a spray area onto which a sanitizer is to be sprayed in accordance with the contact position; and a drive unit spraying the sanitizer onto the spray area determined by an instrument unit provided on the door handle.

In addition, the portion of the hand may be a finger. The finger may be inserted into the door handle in a top-to-bottom direction so that a palm of the hand reaches the inside of the door handle.

In addition, the portion of the hand may be a finger. The finger may be inserted into the door handle in a bottom-to-top direction so that a palm of the hand reaches the inside of the door handle.

In addition, the instrument unit may include two or more nozzles for the spraying of the sanitizer. The two or more nozzles may be air nozzles.

In addition, the first sensor system may be an infrared sensor inclusive of an infrared emitter and an infrared receiver. The infrared emitter may be disposed on one end of an inner surface of the door handle and the infrared receiver may be disposed on the other end of an inner surface of the door handle.

In addition, the second sensor system may include three or more first fiber-optic sensors disposed on an upper area and spaced apart at first distances from each other and three or more second fiber-optic sensors disposed on a lower area spaced apart at the first distances from each other. The three or more second fiber optic sensors may also be spaced apart at second distances from the three or more first fiber-optic sensors, whereby the spray area is formed.

In addition, the two or more nozzles may be disposed in areas defined by the first distances and the second distances, respectively. Each of the two or more nozzles may have a cross shape.

In addition, the instrument unit may further include a first storage tank configured for spraying the sanitizer.

In addition, the instrument unit may further include a second storage tank connected to the first storage tank and configured for executing a cleaning spraying operation before executing the spraying of the sanitizer. The second storage tank may previously store a predetermined amount of the sanitizer by receiving the predetermined amount of the sanitizer from the first storage tank and may include a separate nozzle different from the two or more nozzles.

In addition, the cleaning spraying operation may be executed when the pairing is accomplished, when a third sensor system determines that the occupant has approached within a preset distance after the pairing, or when the third sensor system determines that a portion of a body of the occupant contacts an outer surface of the door handle after the pairing.

In addition, the controller may supply the predetermined amount of the sanitizer to the second storage tank when a detection is accomplished by the first sensor system and execute the spraying of the sanitizer when a detection is accomplished by the second sensor system after the detection is accomplished by the first sensor system.

In addition, when none of the first sensor system and the second sensor system has a recognition depending on whether or not a time in which signal transmission of the second system is stopped is reduced after the detection is accomplished by the second sensor system, the controller may stop the spraying of the sanitizer.

In addition, when a detection time of the second sensor system is reduced after the detection is accomplished by the first sensor system, the controller may stop the spraying of the sanitizer.

In addition, when no detection is accomplished by the first sensor system after the cleaning spraying operation, when a time in which the first sensor system has no recognition is increased and the door is in a locked state, the controller may stop the spraying of the sanitizer.

According to another embodiment, the present disclosure provides a hand sanitizing method for a vehicle. The hand sanitizing method may include: performing, by a communicator, pairing with a smart key; detecting, by a first sensor system, whether or not a portion of a hand of an occupant enters an inside of a door handle after the pairing; detecting, by a second sensor system, a contact position of the portion of the hand in response to the detection of the first sensor system; determining, by a controller, a spray area onto which a sanitizer is to be sprayed in accordance with the contact position; and spraying, by a drive unit, the sanitizer onto the spray area determined by an instrument unit provided on the door handle.

In addition, in the spraying of the sanitizer, the controller may supply a predetermined amount of the sanitizer to a second storage tank when a detection is accomplished by the first sensor system and may execute the spraying of the sanitizer when a detection is accomplished by the second sensor system after the detection is accomplished by the first sensor system.

In addition, in the spraying of the sanitizer, when none of the first sensor system and the second sensor system has a recognition depending on whether or not a time in which signal transmission of the second sensor system is stopped is reduced after the detection is accomplished by the second sensor system, the controller may stop the spraying of the sanitizer.

In addition, in the spraying of the sanitizer, when a detection time of the second sensor system is reduced after the detection is accomplished by the first sensor system, the controller may stop the spraying of the sanitizer.

In addition, the hand sanitizing method may further include stopping, by the controller, the spraying of the sanitizer before the spraying of the sanitizer when a time in which the first sensor system has no recognition is increased and the door is in a locked state when no detection is accomplished by the first sensor system after the cleaning spraying operation.

According to the present disclosure, it is possible to automatically prevent the inside of a vehicle from being contaminated by at least one of bacterium or virus by performing hand sanitization in a typical pattern of behavior of an occupant.

As another effect of the present disclosure, an intelligent vehicle may manage and protect the health of a vehicle occupant.

DESCRIPTION OF SPECIFIC EMBODIMENTS

Advantages and features of the present disclosure, as well as methods of realizing the same, should be more clearly understood from the following detailed description of embodiments when taken in conjunction with the accompanying drawings. However, the present disclosure is not limited to specific embodiments to be described hereinafter but may be embodied in a variety of different forms. Rather, these embodiments are provided so that the description of the present disclosure is complete and fully conveys the scope of the present disclosure to those having ordinary skill in the technical field to which the present disclosure pertains. The present disclosure shall be defined by the scope of the claims. In the drawings, the sizes and relative sizes of layers and areas may be exaggerated for the clarity of explanation.

Throughout this specification, the same reference numerals or signs may be used to designate the same or like components and the expression "and/or" includes each and all combinations of one or more of the items mentioned.

Terms used in this specification are for describing the embodiments and are not intended to limit the present disclosure. In this specification, singular forms are intended to include plural forms unless the context clearly indicates otherwise. Terms, such as "comprise" and/or "include", used in this specification specify the presence of mentioned components, steps, operations, and/or elements but do not preclude the presence or addition of one or more other components, steps, operations, and/or elements.

Although terms, such as first and second, are used to describe a variety of components, it should not be understood that the components are limited thereby. These terms are used merely to distinguish one component from other components. Thus, a first component referred to as first hereinafter may be a second component within the technical idea of the present disclosure.

Unless otherwise defined, all terms (including technical and scientific terms) used in this specification have the same meaning as that commonly understood by those having ordinary skill in the technical field to which the present disclosure pertains. In addition, terms defined in commonly used dictionaries should not be interpreted in an idealized or overly formal sense unless expressly so defined herein. When a component, device, element, or the like of the present disclosure is described as having a purpose or performing an operation, function, or the like, the component, device, or element should be considered herein as being "configured to" meet that purpose or to perform that operation or function.

Hereinafter, a hand sanitizing apparatus and a method for a vehicle according to an embodiment of the present disclosure are described in detail with reference to the accompanying drawings.

Figure 1:
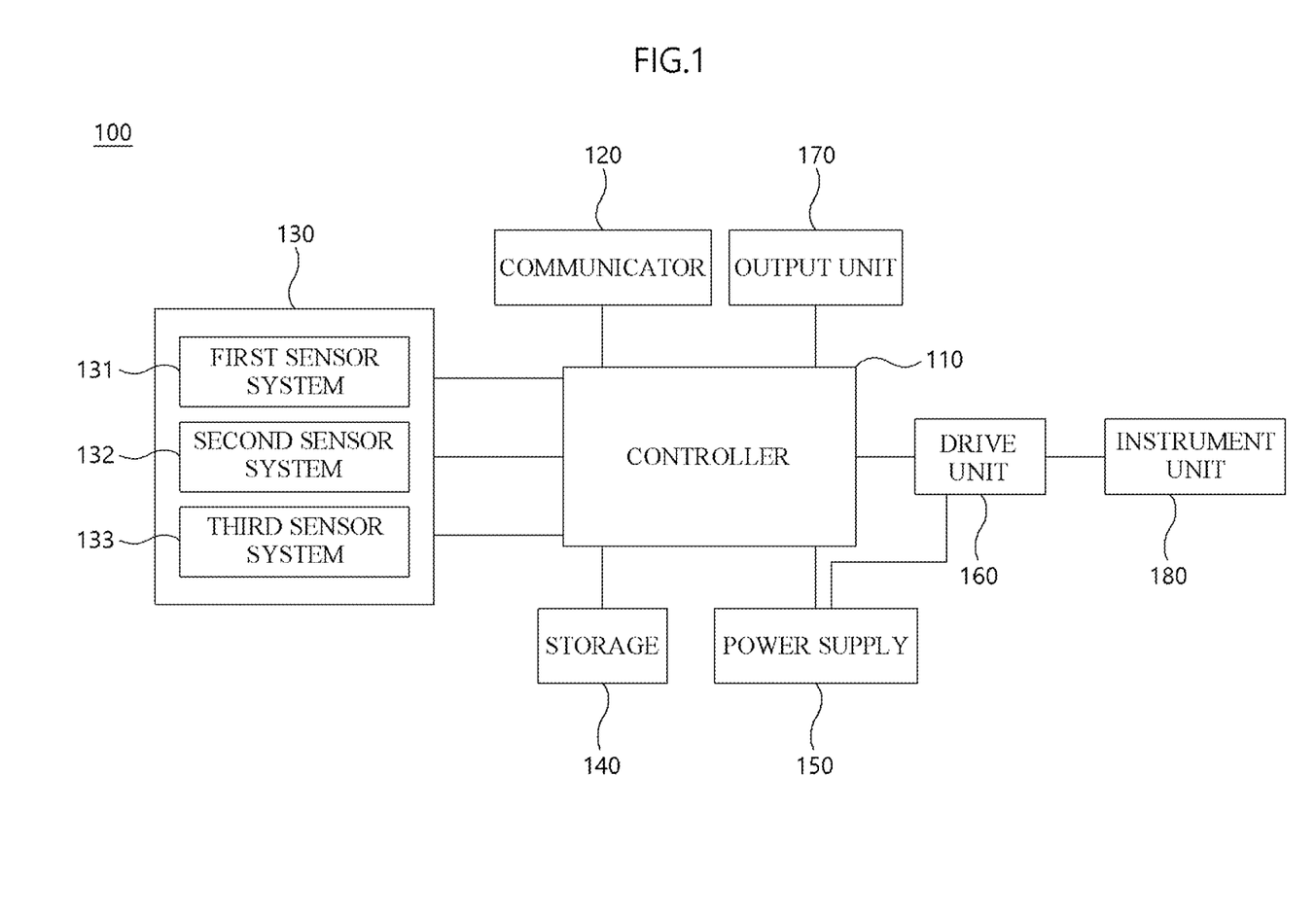
FIG. 1 is a block diagram illustrating a hand sanitizing apparatus according to an embodiment of the present disclosure.

FIG. 1 is a block diagram illustrating a hand sanitizing apparatus 100 according to an embodiment of the present disclosure. Referring to FIG. 1, the hand sanitizing apparatus 100 may include a controller 110 controlling hand sanitizing procedures, a communicator 120 communicating with a smart key (not shown), a sensor block 130 sensing the position of a hand of an occupant (i.e. a concept including a driver and a passenger), a drive unit 160 spraying a sanitizer, an instrument unit 180 including a nozzle ejecting the sanitizer outward, and the like. In addition, the hand sanitizing apparatus 100 may further include a storage 140 storing an algorithm by which a hand sanitizing operation is performed, a power supply 150 supplying power to components, an output unit 170 outputting, for example, information, and the like.

The controller 110 controls the components, such as the communicator 120, the sensor block 130, the storage 140, the power supply 150, the drive unit 160, and the output unit 170, while transmitting and receiving signals thereto and therefrom. In this regard, the controller 110 may be implemented as a microprocessor, a microcontroller, or the like.

The communicator 120 is connected to the smart key (not shown) so as to communicate therewith in order to perform pairing. Short-range wireless communication technology is used for communication access. The short-range wireless communication technology may be implemented as, but not limited to, ultra-wideband (UWB). The short-range wireless communication technology may be Wi-Fi (wireless fidelity), Bluetooth, ZigBee, low frequency (LF) communication, radio frequency (RF) communication, near field communication (NFC), radio-frequency identification (RFID) technology, or the like. In this regard, the communicator 120 may be implemented as a communication circuit, a microprocessor, or the like.

The sensor block 130 includes a first sensor system 131, a second sensor system 132, a third sensor system 133, and the like. The first sensor system 131 performs a function of detecting a portion of the body of the occupant when the portion of the body of the occupant enters the inside of a door handle (i.e. the occupant may place a hand in the door handle). In this regard, the first sensor system 131 may include a plurality of infrared (IR) sensors performing rapid sensing without malfunctions. The IR sensors are advantageous considering that the inside of the door handle is dark.

The second sensor system 132 performs a function of determining a spray area onto which a sanitizer is to be sprayed after a signal of the first sensor system 131 has been recognized. In this regard, the second sensor system 132 classifies contact positions to which the portion of the body of the occupant comes into contact. In other words, the contact positions may be classified as upper, lower, left, middle, and right positions depending on the grip type, i.e., hand position, orientation, and the like.

The third sensor system 133 performs a function of detecting the occupant approaching the vehicle. More specifically, the third sensor system 133 performs a function of detecting the occupant when the occupant has entered an area within a predetermined distance from the vehicle. In this regard, the third sensor system 133 may include a plurality of camera sensors, a plurality of distance sensors, and the like. In other words, the sensors of the third sensor system 133 may be disposed on, for example, the front surface, the rear surface, and side surfaces of the vehicle. As a sensor of the third sensor system 133 disposed on the front surface, a camera disposed on a navigation device or a black box may be used.

In addition, the third sensor system 133 may be implemented as touch sensors. Thus, when a portion of the body of the occupant comes into contact with the door handle, the sanitizer may be sprayed. In this regard, a touch sensor may be disposed on the outer surface of the door handle.

The storage 140 performs a function of storing a program, data, software, or the like having an algorithm by which whether or not the portion of the body of the occupant has entered the door handle is detected and the sanitizer is sprayed. The storage 140 may include at least one type of storage medium from among a flash memory, a hard disk, a multimedia card-type micro memory, a card type memory (e.g., a secure digital (SD) memory or an extreme digital (XD) memory), a random access memory (RAM), a static random access memory (SRAM), a read only memory (ROM), an electrically erasable programmable read only memory (EEPROM), a programmable read only memory (PROM), a magnetic memory, a magnetic disk, and optical disk.

The power supply 150 performs a function of supplying power to the components. Thus, the power supply 150 may be a battery pack comprised of rechargeable battery cells, a lead acid battery, or the like. In addition, the power supply 150 may include a direct current-direct current (DC-DC) converter, an inverter, a regulator, or the like.

The drive unit 160 performs a function of spraying the sanitizer under the control of the controller 110. In this regard, the drive unit 160 may include a small motor pump, an electronic circuit, or the like.

The output unit 170 performs a function of outputting data to be processed to the controller 110. Of course, a setup screen displaying settings regarding the operation of spraying the sanitizer may be output. The settings on the setup screen may include an on/off setting for a sanitizer spray function, a reservation setting for the on/off setting, a sanitizer spray execution time setting for this purpose, and the like.

The output unit 170 may be a liquid crystal display (LCD), a light-emitting diode (LED) display, an organic LED (OLED) display, a touchscreen, a flexible display, a head-up display (HUD), or the like. A touchscreen may also be used as an input means. Of course, the output unit 170 may be implemented as a sound system that performs at least one of data input and data output using voice, sound, and the like.

The instrument unit 180 may be a nozzle (not shown) disposed on a handle grip (not shown), a storage tank (not shown) storing the sanitizer, or the like. The nozzle may be formed integrally with a tube (not shown) or may be formed separately from the tube and disposed on a distal end of the tube.

Figure 2:
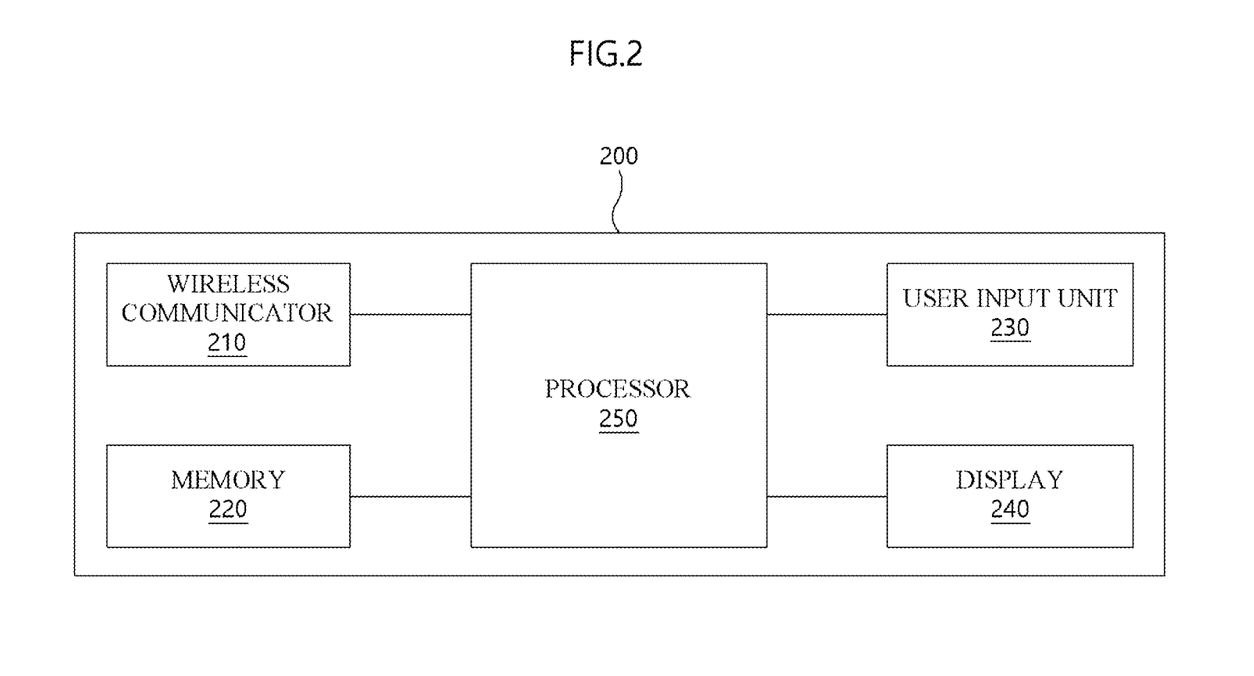
FIG. 2 is a block diagram illustrating a typical smart key.

FIG. 2 is a block diagram illustrating a typical smart key 200. Referring to FIG. 2, the smart key 200 is a remote control able to remotely control the vehicle (not shown). The smart key 200 may be implemented as a key fob, keyless go card, a smartphone, or the like.

The smart key 200 may include a wireless communicator 210, a memory 220, a user input unit 230, a display 240, and a processor 250.

The wireless communicator 210 establishes a communication connection with the communicator 120 of the vehicle. The memory 220 may store identification information, such as personal identification number (PIN). In addition, the memory 220 may store software programmed such that the processor 250 performs a predetermined operation. In addition, the memory 220 may store information (i.e. data) transmitted from the vehicle via the communicator 120.

The user input unit 230 may generate data in response to a user manipulation. For example, the user input unit 230 generates a control instruction, such as "vehicle door unlock" or "engine start," in response to a user input. The user input unit 230 may be implemented as at least one from among a keyboard, a keypad, buttons, switches, a touchpad, a touchscreen, and the like.

The display 240 outputs progress states and results according to the operation of the processor 250. The display 240 may be implemented as at least one from among a liquid crystal display (LCD), a thin film transistor-liquid crystal display (TFT LCD), an organic light-emitting diode (OLED) display, a flexible display, a three-dimensional (3D) display, a transparent display, a touchscreen, and the like.

The processor 250 controls the overall operation of the smart key 200. The processor 250 may be implemented as including a microprocessor, an electronic circuit, or the like. In particular, the processor 250 attempts pairing for communication connection to the communicator 120.

Figure 3:
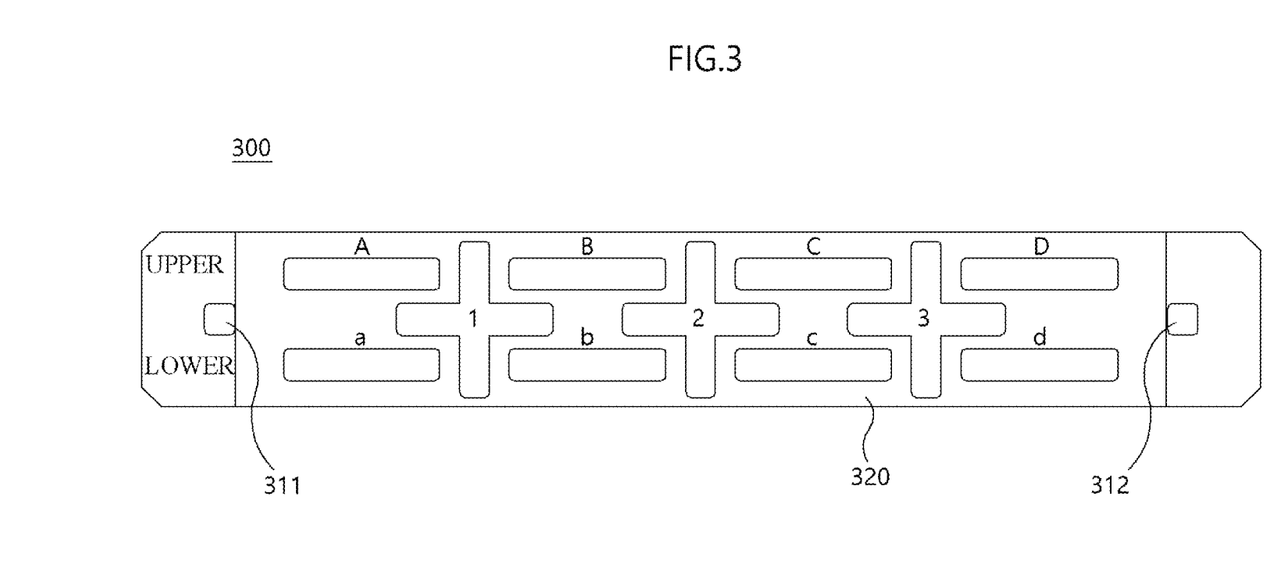
FIG. 3 is a view illustrating the inner surface of a door handle according to an embodiment of the present disclosure.

FIG. 3 is a view illustrating the inner surface of a door handle 300 according to an embodiment of the present disclosure. Referring to FIG. 3, the door handle 300 includes an IR emitter 311 and an IR receiver 312 spaced apart at a predetermined distance from the IR emitter 311. The IR emitter 311 and the IR receiver 312 are disposed at middle positions of the inner surface of the door handle 300 in the longitudinal direction. In addition, the IR emitter 311 and the IR receiver 312 belong to the first sensor system (131 in FIG. 1).

In addition, (1-2)th to (1-4)th fiber-optic sensors A, B, C, and D are disposed in the upper area between the IR emitter 311 and the IR receiver 312, spaced apart at predetermined distances from each other, and (2-1)th to (2-4)th fiber-optic sensors a, b, c, and d are disposed in the lower area between the IR emitter 311 and the IR receiver 312, spaced apart at predetermined distances from each other.

In addition, the (1-2)th to (1-4)th fiber-optic sensors A, B, C, and D are spaced apart at predetermined distances from the (2-1)th to (2-4)th fiber-optic sensors a, b, c, and d, respectively. First to third nozzles 1, 2, and 3 are disposed between the (1-2)th to (1-4)th fiber-optic sensors A, B, C, and D and the (2-1)th to (2-4)th fiber-optic sensors a, b, c, and d. The first to third nozzles 1, 2, and 3 are air nozzles each having the shape of a cross. Although only the nozzles are illustrated in FIG. 3 for the convenience of understanding, each of the nozzles may include a nozzle body (not shown) and a jet orifice (not shown) formed in the surface of the nozzle body.

The (1-2)th to (1-4)th fiber-optic sensors A, B, C, and D, the (2-1)th to (2-4)th fiber-optic sensors a, b, c, and d, and the first to third nozzles 1, 2, and 3 are inserted into and disposed in the surface of a rear plate 320. The rear plate 320 may be made of a metal material, a plastic material, or the like. For this inserted disposition, an insertion recess (not shown) is formed in the surface of the rear plate 320.

Figure 4:
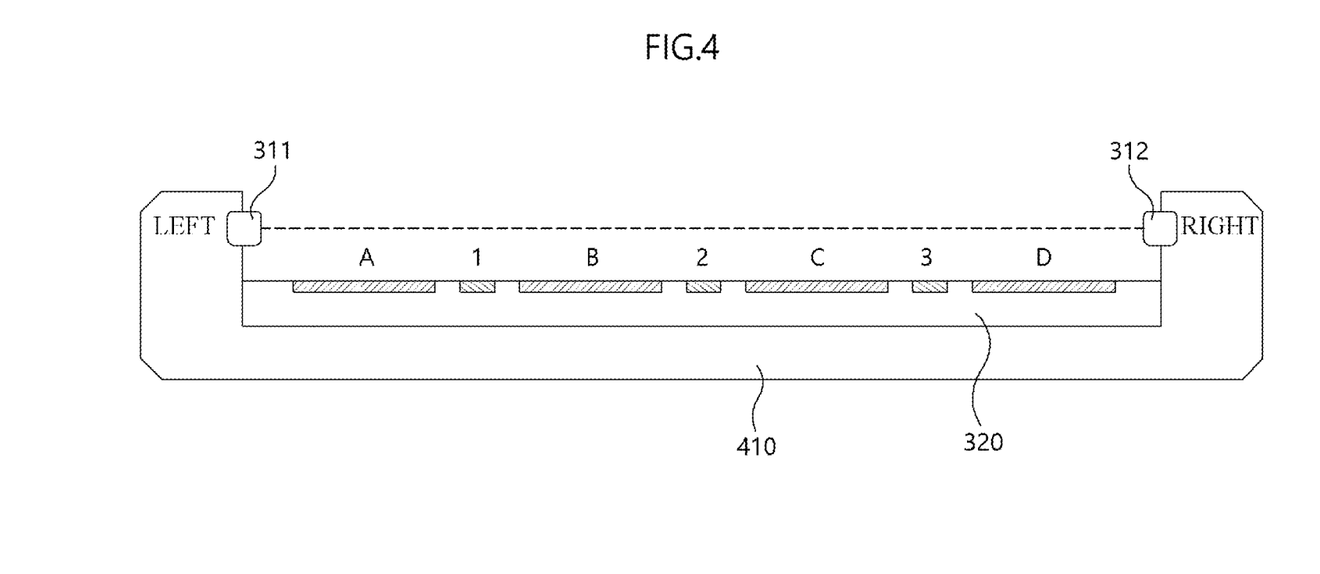
FIG. 4 is a plan view of the door handle illustrated in FIG. 3.

FIG. 4 is a plan view of the door handle 300 illustrated in FIG. 3. Referring to FIG. 4, the door handle 300 includes a door handle body 410 and the rear plate 320 disposed on the bottom within the door handle body 410. The door handle body 410 has a U-shaped cross-section. The IR emitter 311 and the IR receiver 312 are disposed on both ends of the inside of this shape. Thus, IR radiation travels from left to right as indicated with a dotted arrow. In this state, when the hand of the occupant enters the inside of the door handle body 410, the IR radiation is stopped and the controller 110 may detect the stopping of the IR radiation.

Figure 5:
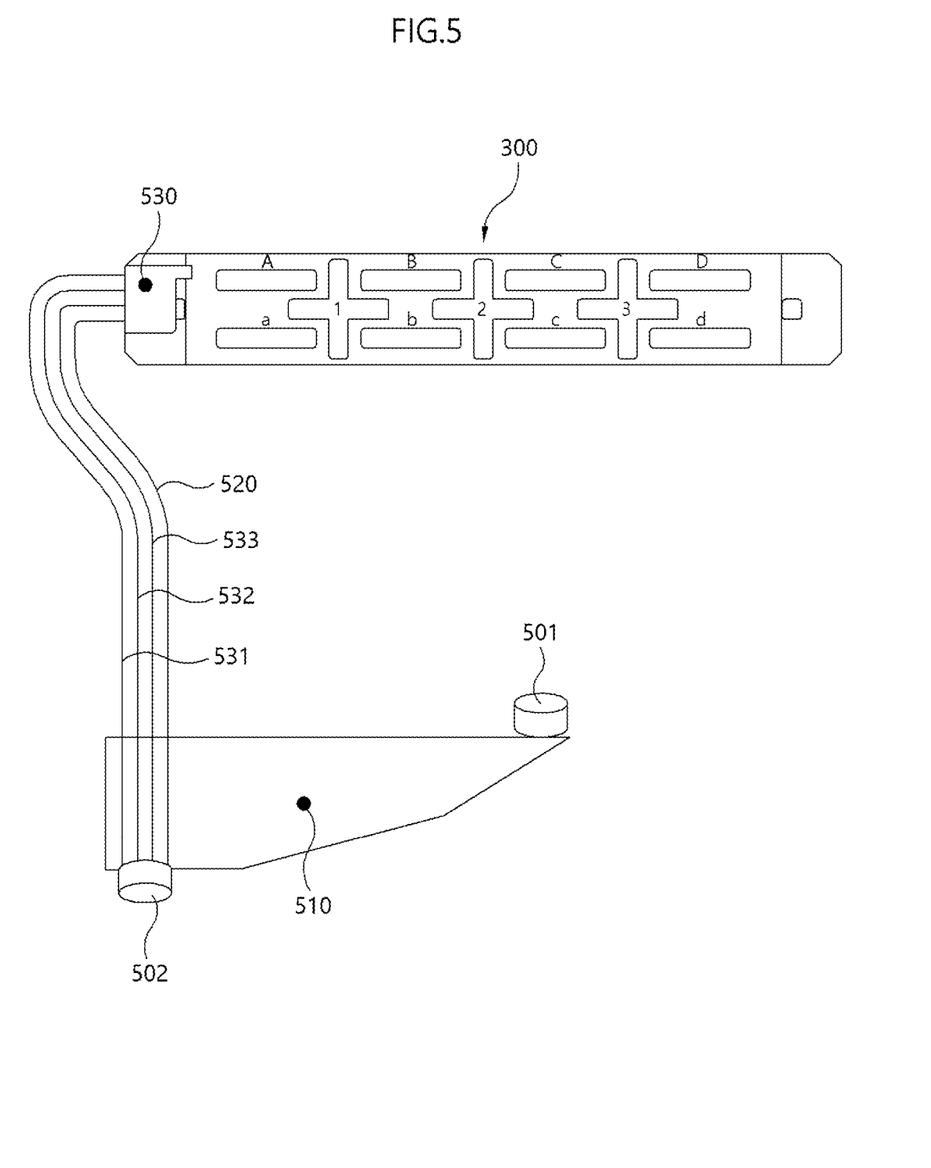
FIG. 5 is a conceptual view of the instrument unit illustrated in FIG. 1.

FIG. 5 is a conceptual view of the instrument unit 180 illustrated in FIG. 1. Referring to FIG. 5, the instrument unit 180 may include a first storage tank 510 storing the sanitizer, a second storage tank 530 configured for small amount cleaning before the use of the first sensor system 131 and the second sensor system 132, first to third nozzles 1, 2, and 3, and the like. The first to third nozzles 1, 2, and 3 are connected to first to third tubes 531, 532, and 533, respectively. A motor pump (not shown) may be provided on a distal end or a middle portion of each of the first to third tubes 531, 532, and 533. The designed position of the motor pump may vary depending on the design.

The first storage tank 510 may be provided integrally on the surface of the bottom of a door armrest (not shown). An inlet 501 is provided on the top portion of the first storage tank 510 and an outlet 502 is provided on the bottom portion of the first storage tank 510. In addition, the second storage tank 530 is provided on the door handle body 410 of the door handle 300. The second storage tank 530 is connected to the first storage tank 510 through a tube 520 and has a predetermined amount of sanitizer previously contained therein.

The first storage tank 510 is also connected to the first to third nozzles 1, 2, and 3. Thus, the sanitizer is sprayed for cleaning before the hand of the occupant is recognized according to the following conditions.

① A welcome signal is generated in response to the smart key 200 and the communicator 120 being paired:

When the pairing is established due to an approach at a distance of 10 m or less, a target may be recognized due to UWB wakeup.

② The third sensor system detects the occupant having approached at a preset distance or less:

In this case, the third sensor system is a camera sensor, a distance sensor, or the like. The preset distance may be about 1 m or less. Of course, in this case, a welcome signal is also generated.

③ A case in which a portion of the body of the occupant contacting the outer surface of the door handle is detected by the third sensor system (in which case, the third sensor system is a touch sensor):

A sanitizer spraying structure is disposed inside the door handle 300, such that the sanitizer is sprayed to the palm instead of the back of the hand. This may prevent the sanitizer from being sprayed to other places than the handle or places in which the hand is not present and thus prevent the sanitizer from flowing down.

Figure 6:
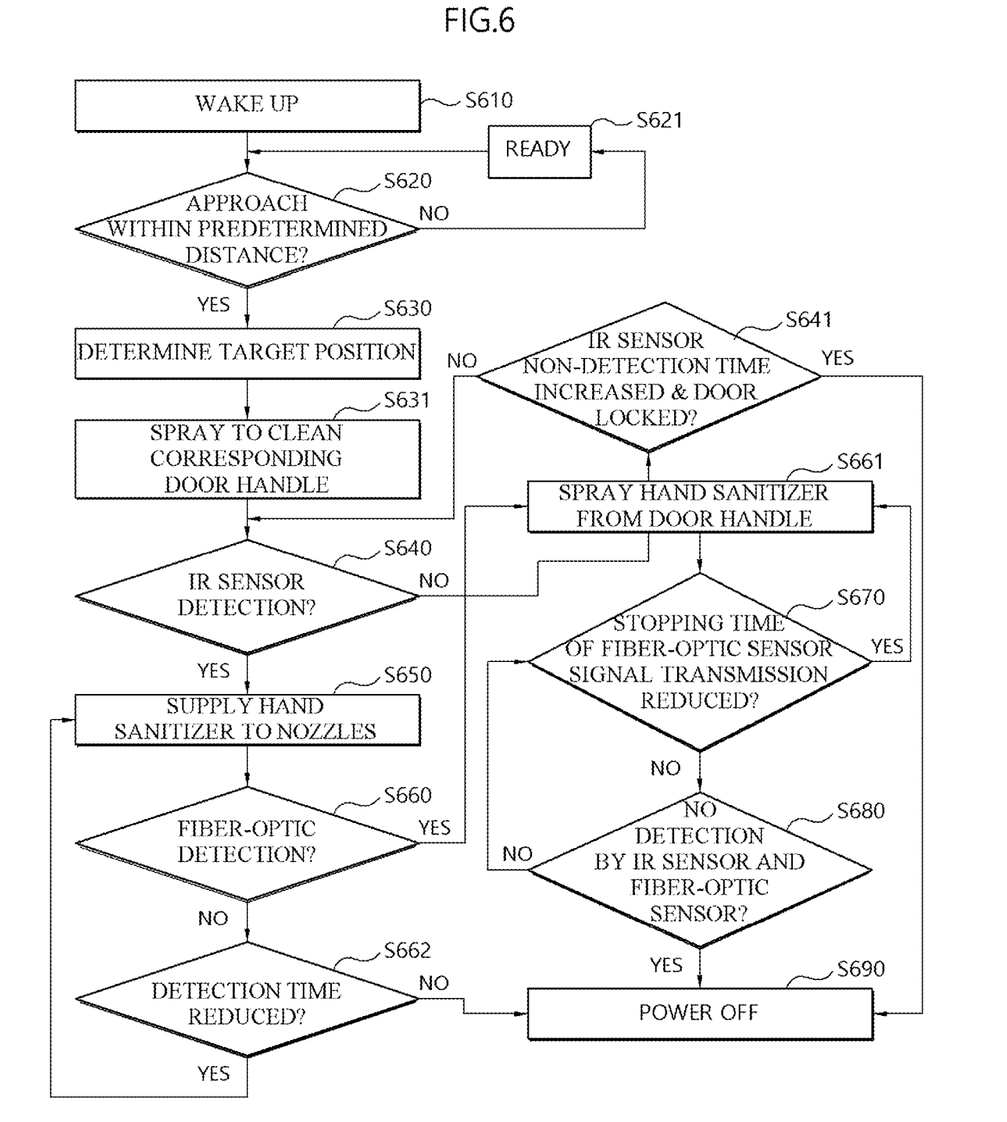
FIG. 6 is a flowchart illustrating a process of ejecting a sanitizer according to an embodiment of the present disclosure.

FIG. 6 is a flowchart illustrating a process of ejecting the sanitizer according to an embodiment of the present disclosure. Referring to FIG. 6, when the smart key 200 approaches the vehicle and enters the range of communication, the smart key 200 is paired with the communicator 120 and the controller 110 is woken up in step S610.

When the controller 110 is woken up, whether or not the occupant holding the smart key 200 approaches within a predetermined distance (e.g., about 1 m) is determined in step S620.

When the occupant is determined within the predetermined distance in the step S620, the target position of the occupant is determined in step S630 and a spraying operation for cleaning the door handle 300 is performed in step S631.

On the contrary, when the occupant is determined not to be within the predetermined distance in the step S620, the controller 110 maintains a standby mode state in step S621. Afterwards, the step S620 is performed.

After the spraying operation for cleaning the door handle 300 is performed, whether or not a portion of the body of the occupant is detected by the IR sensors, such as the IR emitter 311 and the IR receiver 312, is determined in step S640. In other words, whether or not a hand of the occupant has entered the inside of the door handle 300 is determined.

When the portion of the body of the occupant is detected by the IR sensors in the step S640, the controller 110 supplies a small amount of a sanitizer to the second storage tank 530 via the drive unit 160 in step S650. The amount of the sanitizer contained in the second storage tank 530 is a portion of the amount of sanitizer contained in the first storage tank 510.

Afterwards, whether or not the shape or orientation of the grip of the occupant is detected by the fiber-optic sensors A, B, C, D, a, b, c, and d is determined in step S660.

When the shape or orientation of the grip is not detected in the step S660, whether or not the detection time of the IR sensors is reduced is determined in step S662. When the detection time (ms) of the IR sensors is determined as not reduced, i.e., NO in the step S662, then step S650 is performed. On the contrary, when the detection time of the IR sensors is determined to be reduced, i.e., YES in the step S662, then power off is accomplished in step S690.

In addition, when the portion of the body of the occupant is not detected by the IR sensors in the step S640, whether or not two conditions are met is determined in step S641. In other words, the step S641 determines whether or not a time in which the portion of the body of the occupant has not been detected by the IR sensors is increased and whether or not the door is locked. When both the two conditions are met in the step S641, the power off is accomplished in the step S690. In other words, the operation of spraying the sanitizer is stopped.

On the contrary, when none of the two conditions are met in the step S641, the step S640 is performed again.

In addition, when the detection is not accomplished by the fiber-optic sensors in the step S660, the sanitizer is sprayed in step S661.

Afterwards, it is determined whether or not a period (s) in which signal transmission of the fiber-optic sensors is stopped is reduced in step S670. As a result of the determination, when the period (s) in which signal transmission of the fiber-optic sensors is stopped is reduced in the step S670, the step S661 is performed. On the contrary, when the period (s) in which signal transmission of the fiber-optic sensors is stopped is not reduced in the step S670, whether or not none of the IR sensors and the fiber-optic sensors has a recognition is determined in step S680.

As a result of the determination, when none of the IR sensors and the fiber-optic sensors is determined to have a recognition in the step S680, the power off is accomplished in the step S690. On the contrary, when any of the IR sensors and the fiber-optic sensors is determined to have a recognition in the step S680, the step S670 is performed. Specifically, the fiber-optic sensor signal is continuously transmitted depending on the time in which the door handle 300 is held, and thus, the sanitizer is also continuously ejected.

Figure 7:
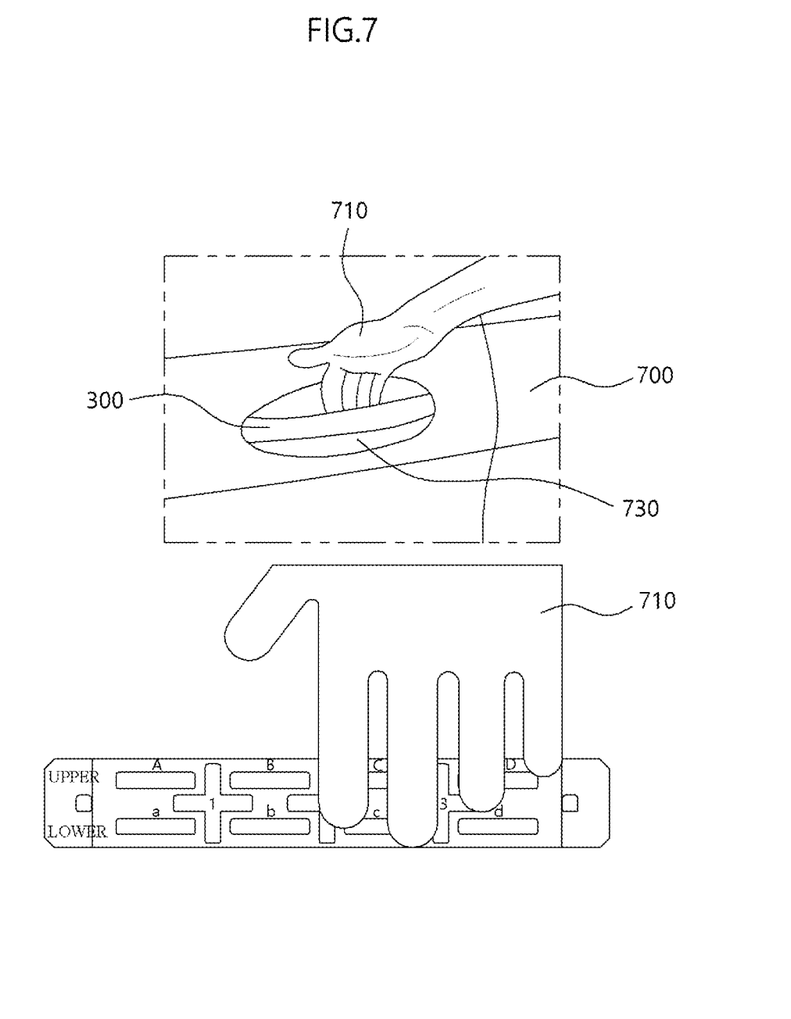
FIGS. 7-9 are conceptual views illustrating spray area recognition and spray amount determination according to a variety of grip orientations.
Figure 8:
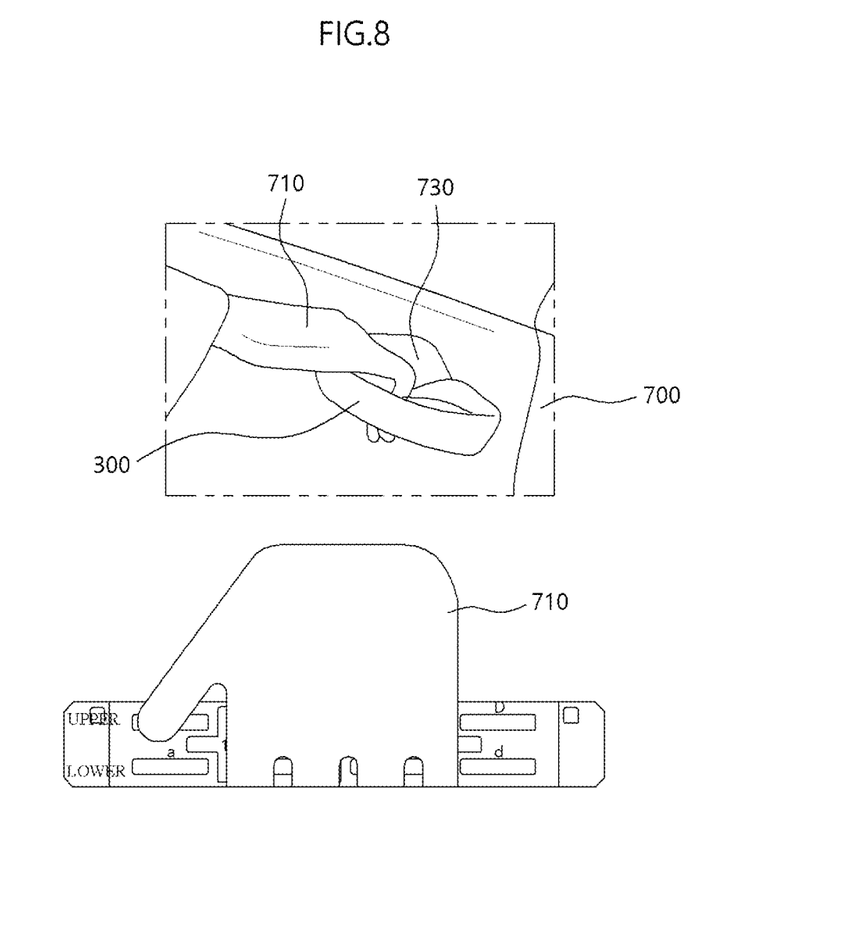
Figure 9:
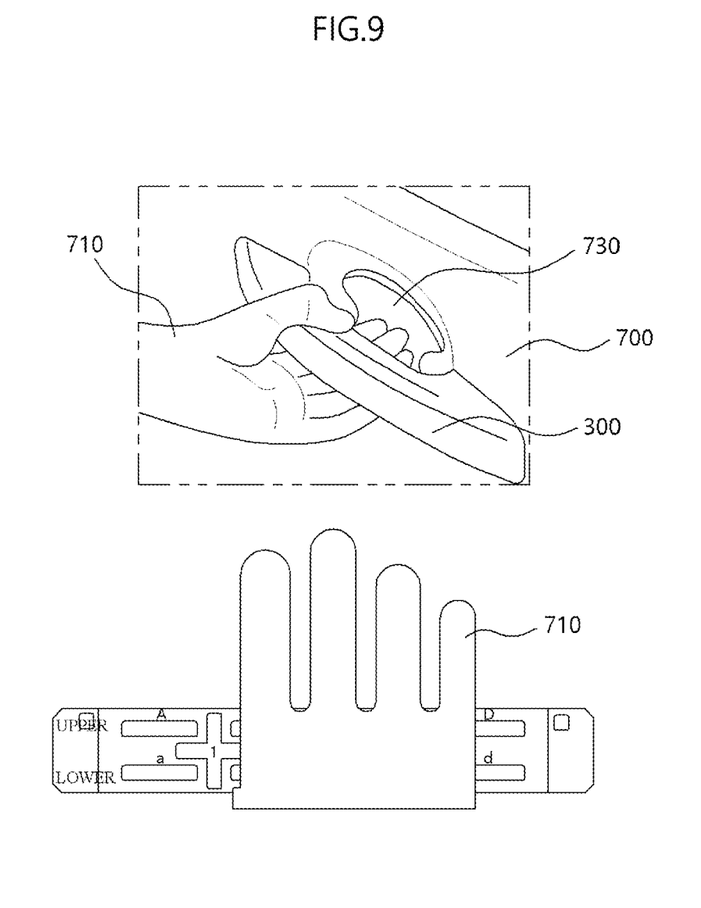

FIGS. 7-9 are conceptual views illustrating spray area recognition and spray amount determination according to a variety of grip shapes. In each of FIGS. 7-9, the upper portion is a photograph in which an actual hand has entered the inside of a door handle, while the lower portion illustrates a concept in which the hand is located inside the door handle.

In the case of FIG. 7, when a hand 710 (more specifically, fingers) enters the inside of the door handle 300 formed in a door 730 of a vehicle 700 in a direction from above the door handle 300, the fiber-optic sensors serving as contact points are the fiber-optic sensors C, c, and D. In this case, the nozzles corresponding to a spray area are the nozzles 2 and 3. In other words, the spray area is the right spray area.

In the case of FIG. 8, the fiber-optic sensors serving as contact points are the fiber-optic sensors A, B, b, C, and c. In this case, the nozzles corresponding to a spray area are the nozzles 1 and 2. In FIG. 8, the fingers are inserted into the door handle 300 in the top-to-bottom direction, so that the palm reaches the inner surface of the door handle 300.

In the case of FIG. 9, the fiber-optic sensors serving as contact points are the fiber-optic sensors A, b, c, and d. In this case, the nozzles corresponding to a spray area are the nozzles 1, 2, and 3. In FIG. 9, the fingers are inserted into the door handle 300 in the bottom-to-top direction, so that the palm reaches the inner surface of the door handle 300.

As illustrated in FIGS. 7-9, the contact positions may be classified as the upper, lower, left, middle, and right positions depending on the grip type by using N number of fiber-optic sensors in the determination of a touch area. Thus, pressure is applied to the door handle in a variety of grip types. Spray areas are classified according to the grip types, and nozzles are selected according to the spray areas, respectively. Accordingly, the sanitizer may be accurately sprayed.

In addition, according to this structure, signals are transmitted by the fiber-optic sensors depending on the time during which the door handle is held, and thus, the sanitizer is also continuously sprayed. In other words, when the sanitizer is sprayed during the time in which signals are transmitted by the fiber-optic sensors, a phenomenon in which the sanitizer is sprayed even when no hand is present inside the door handle may be prevented.

In addition, the nozzles for spraying the sanitizer are disposed inside the door handle so as to spray the sanitizer toward the palm instead of the back of the hand. It is possible to prevent the sanitizer from being sprayed to other places than the handle or places in which the hand is not present and thus the sanitizer from flowing down.

Although the door provided on the driver's seat side has mainly been described with reference to FIGS. 7-9, the hand sanitizing apparatus for a vehicle described with reference to FIGS. 1-6 may be applied to any doors provided in vehicles.

In addition, the steps of the method or the algorithm described with respect to the embodiments disclosed herein may be realized in the form of program instructions executable by a variety of computing means, such as a microprocessor, a processor, or a central processing unit (CPU), and be recorded in a computer readable recording medium. The computer readable recording medium may include program (instruction) codes, data files, data structures, or the like, alone or in combination.

The program (instruction) codes recorded in the medium may be specially designed and configured for the present disclosure or may be publicly known and available to those having ordinary skill in the technical field of computer software. Examples of the computer readable recording medium may include magnetic media, such as hard disks, floppy disks and magnetic tapes; optical media, such as compact disc read-only memories (CD-ROMs), digital versatile discs (DVDs), and Blu-ray discs; and semiconductor memory devices, such as read-only memories (ROMs), random access memories (RAMs), and flash memories, specially configured to store and execute program (instruction) codes.

An example of the program (instruction) codes includes not only machine language codes made by a compiler but also high-level language codes executable by a computer using an interpreter. Hardware devices as described above may be configured as operate as one or more software modules in order to perform the operation of the present disclosure, and vice versa.

What is claimed is:

1. A hand sanitizing apparatus for a vehicle, the hand sanitizing apparatus comprising:

a communicator performing pairing with a smart key;
a first sensor system detecting whether or not a portion of a hand of an occupant enters an inside of a door handle after the pairing;
a second sensor system detecting a contact position of the portion of the hand in response to the detection of the first sensor system;
a controller determining a spray area onto which a sanitizer is to be sprayed in accordance with the contact position; and
a drive unit spraying the sanitizer onto the spray area determined by an instrument unit provided on the door handle.

2. The hand sanitizing apparatus of claim 1, wherein the portion of the hand is a finger, and the finger is inserted into the door handle in a top-to-bottom direction so that a palm of the hand reaches the inside of the door handle.

3. The hand sanitizing apparatus of claim 1, wherein the portion of the hand is a finger, and the finger is inserted into the door handle in a bottom-to-top direction so that a palm of the hand reaches the inside of the door handle.

4. The hand sanitizing apparatus of claim 1, wherein the instrument unit comprises two or more nozzles for the spraying of the sanitizer, the two or more nozzles being air nozzles.

5. The hand sanitizing apparatus of claim 4, wherein the first sensor system is an infrared sensor comprised of an infrared emitter and an infrared receiver, the infrared emitter being disposed on one end of an inner surface of the door handle, and the infrared receiver being disposed on the other end of an inner surface of the door handle.

6. The hand sanitizing apparatus of claim 5, wherein the second sensor system comprises three or more first fiber-optic sensors disposed on an upper area and spaced apart first distances from each other and three or more second fiber-optic sensors disposed on a lower area, spaced apart the first distances from each other, and spaced apart second distances from the three or more first fiber-optic sensors, whereby the spray area is formed.

7. The hand sanitizing apparatus of claim 6, wherein the two or more nozzles are disposed in areas defined by the first distances and the second distances, respectively, and each of the two or more nozzles has a cross shape.

8. The hand sanitizing apparatus of claim 4, wherein the instrument unit further comprises a first storage tank configured for the spraying of the sanitizer.

9. The hand sanitizing apparatus of claim 8, wherein the instrument unit further comprises a second storage tank connected to the first storage tank and configured for execution of a cleaning spraying operation before execution of the spraying of the sanitizer, wherein the second storage tank previously stores a predetermined amount of the sanitizer by receiving the predetermined amount of the sanitizer from the first storage tank and includes a separate nozzle different from the two or more nozzles.

10. The hand sanitizing apparatus of claim 9, wherein the cleaning spraying operation is executed when the pairing is accomplished, when a third sensor system determines that the occupant has approached within a preset distance after the pairing, or when the third sensor system determines that a portion of a body of the occupant contacts an outer surface of the door handle after the pairing.

11. The hand sanitizing apparatus of claim 9, wherein the controller supplies the predetermined amount of the sanitizer to the second storage tank when a detection is accomplished by the first sensor system and executes the spraying of the sanitizer when a detection is accomplished by the second sensor system after the detection is accomplished by the first sensor system.

12. The hand sanitizing apparatus of claim 11, wherein, when none of the first sensor system and the second sensor system has a recognition depending on whether or not a time in which signal transmission of the second system is stopped is reduced after the detection is accomplished by the second sensor system, the controller stops the spraying of the sanitizer.

13. The hand sanitizing apparatus of claim 11, wherein, when a detection time of the second sensor system is reduced after the detection is accomplished by the first sensor system, the controller stops the spraying of the sanitizer.

14. The hand sanitizing apparatus of claim 9, wherein, when no detection is accomplished by the first sensor system after the cleaning spraying operation, when a time in which the first sensor system has no recognition is increased and the door is in a locked state, the controller stops the spraying of the sanitizer.

15. A hand sanitizing method for a vehicle, the hand sanitizing method comprising:
performing, by a communicator, pairing with a smart key;
detecting, by a first sensor system, whether or not a portion of a hand of an occupant enters an inside of a door handle after the pairing;
detecting, by a second sensor system, a contact position of the portion of the hand in response to the detection of the first sensor system;
determining, by a controller, a spray area onto which a sanitizer is to be sprayed in accordance with the contact position; and
spraying, by a drive unit, the sanitizer onto the spray area determined by an instrument unit provided on the door handle.

16. The hand sanitizing method of claim 15, wherein the instrument unit comprises two or more nozzles for the spraying of the sanitizer, the two or more nozzles being air nozzles.

17. The hand sanitizing method of claim 16, wherein the instrument unit further comprises a first storage tank configured for the spraying of the sanitizer.

18. The hand sanitizing method of claim 16, wherein the instrument unit further comprises a second storage tank connected to the first storage tank and configured for execution of a cleaning spraying operation before execution of the spraying of the sanitizer, wherein the second storage tank previously stores a predetermined amount of the sanitizer by receiving the predetermined amount of the sanitizer from the first storage tank and includes a separate nozzle different from the two or more nozzles.

19. The hand sanitizing method of claim 18, wherein, in the spraying of the sanitizer, the controller supplies the predetermined amount of the sanitizer to the second storage tank when a detection is accomplished by the first sensor system and stops the spraying of the sanitizer when a detection is accomplished by the second sensor system after the detection is accomplished by the first sensor system.

20. The hand sanitizing method of claim 19, wherein, in the spraying of the sanitizer, when none of the first sensor system and the second sensor system has a recognition depending on whether or not a time in which signal transmission of the second sensor system is stopped is reduced after the detection is accomplished by the second sensor system, the controller stops the spraying of the sanitizer.

* * * * *